United States Patent [19]

Mansbach et al.

[11] 4,300,907
[45] Nov. 17, 1981

[54] SERUM VITAMIN $B_{12}$ ASSAY AND KIT THEREFOR

[75] Inventors: Lillian Mansbach, New City; Henry McCarter, Pine Island, both of N.Y.

[73] Assignee: Becton, Dickinson and Company, Paramus, N.J.

[21] Appl. No.: 118,583

[22] Filed: Feb. 4, 1980

[51] Int. Cl.³ .................... G01N 33/82; G01N 33/58
[52] U.S. Cl. ................... 23/230 B; 23/230.3; 422/61; 424/1
[58] Field of Search ............... 23/230 B, 230.3, 230.6; 422/61; 424/1

[56] References Cited

U.S. PATENT DOCUMENTS

| | | | |
|---|---|---|---|
| 3,937,799 | 2/1976 | Lewin | 424/1 |
| 3,980,764 | 9/1976 | Adams | 424/1 |
| 4,028,465 | 6/1977 | Lewin | 424/1 |
| 4,167,556 | 9/1979 | Selhub | 424/1 |
| 4,188,189 | 2/1980 | Allen | 23/230 BX |

OTHER PUBLICATIONS

J. I. Toohey, et al., J. Biol. Chem., 236(2), 560–563 (1961).
W. A. Fenton, et al., Anal Biochem., 90(1), 119–125 (1978).

*Primary Examiner*—Sidney Marantz
*Attorney, Agent, or Firm*—Louis E. Marn; Elliot M. Olstein

[57] ABSTRACT

In a vitamin $B_{12}$ assay, serum, containing vitamin $B_{12}$ bound to endogenous binders therefor, is released from such endogenous binders by a releasing agent comprised of a water miscible organic liquid, such as, acetone, reducing agent and cyanide ions. Such release can be effected at room temperature, as compared to prior procedures which required heating to elevated temperatures.

32 Claims, No Drawings

SERUM VITAMIN $B_{12}$ ASSAY AND KIT THEREFOR

This invention relates to the release of serum vitamin $B_{12}$ from endogenous binders therefor, and more particularly, to an improved assay and kit for vitamin $B_{12}$.

Currently, vitamin $B_{12}$ is measured by a competitive protein binding technique. In brief, competitive protein binding for the assay of vitamin $B_{12}$ involves the ability of unlabeled vitamin $B_{12}$ in serum or other media to compete with labeled vitamin $B_{12}$ for a specific vitamin $B_{12}$ binder, and thereby inhibit the binding of labeled vitamin $B_{12}$. As a result of the competitive inhibition, the ratio of bound labeled vitamin $B_{12}$ to free labeled vitamin $B_{12}$ diminishes as the concentration of unlabeled vitamin $B_{12}$ is increased. Accordingly, the concentration of vitamin $B_{12}$ in an unknown sample; e.g., a patient's serum, is obtained by comparing the inhibition observed with that produced by known amounts of vitamin $B_{12}$, as presented in a standard curve. In determining vitamin $B_{12}$ in a serum, it is necessary to initially release the vitamin $B_{12}$ from endogenous binders therefor. Currently, such a release is effected by heating the serum to elevated temperatures for a period of time; e.g., temperature in the order of about 100° C. for about 15 minutes or longer. Such heating increases the length of the assay, necessitates the use of a water bath, and in addition requires cooling before the competitive protein binding technique can be initiated.

In accordance with one aspect of the present invention, serum vitamin $B_{12}$ is released from endogenous binders therefor by use of a liquid releasing agent which includes an organic liquid, which does not destroy vitamin $B_{12}$, a reducing agent which does not destroy vitamin $B_{12}$, and cyanide ions.

In accordance with another aspect of the present invention, there is provided an improved assay for vitamin $B_{12}$ in a serum wherein the vitamin $B_{12}$ is released from endogenous binders by the use of a liquid releasing agent which includes an organic liquid which does not destroy vitamin $B_{12}$, a reducing agent which does not destroy vitamin $B_{12}$ and cyanide ions.

In accordance with a further aspect of the present invention there is provided a kit for the assay of vitamin $B_{12}$ which includes vitamin $B_{12}$ tracer, vitamin $B_{12}$ binder and a liquid releasing agent for releasing vitamin $B_{12}$ from endogenous binders which is comprised of an organic liquid which does not destroy vitamin $B_{12}$, a reducing agent which does not destroy vitamin $B_{12}$, and cyanide ions.

Applicant has found that by the use of a liquid releasing agent in accordance with the invention it is possible to release vitamin $B_{12}$ from endogenous serum proteins without using the elevated temperatures heretofore required to effect heat release of the vitamin $B_{12}$. Thus, vitamin $B_{12}$ can be released from endogenous binder at temperatures lower than 100° C.; e.g., it is possible to effect heat release at room temperature, although higher temperatures could be employed.

The organic liquids which are used in the $B_{12}$ releasing agent of the present invention are preferably water miscible to facilitate the subsequent assay. In addition, the organic liquid should be one which when diluted in the subsequent assay does not materially affect the $B_{12}$ binding capacity of the $B_{12}$ binder employed in the assay; i.e., the binder is capable of providing sufficient $B_{12}$ binding capacity in the presence of the assay diluted organic liquid to provide an effective $B_{12}$ assay. The organic liquid is generally one of which is known in the art to be suitable for use as a water miscible organic solvent. As representative examples of suitable organic liquids, there may be mentioned: ketones, such as acetone; alcohols; in particular alkanols such as methanol, ethanol, etc., ethers, such as dioxane, tetrahydrofuran, etc.; and miscellaneous liquids such as dimethylformamide, dimethylsulfoxide, etc. It is to be understood that the releasing agent may include one or more of such organic liquids. The selection of a particular liquid is deemed to be within the scope of those skilled in the art from the teachings herein.

The reducing agent employed as one of the components of the vitamin $B_{12}$ releasing agent may be either an organic or inorganic reducing agent which does not destroy vitamin $B_{12}$. As representative examples of suitable reducing agents there may be mentioned: dithiothreitol, dithioerythritol, monothioglycol, thiodiglycol, thioglycollic acid, cysteine, homocysteine, glutathione, mercaptoethanol, sulfhydryl reducing agents or inorganic reducing agents such as sodium sulfite, sodium dithionate, sodium sulfide, sodium metabisulfite, with the organic reducing agents being preferred. The reducing agent component could be a reducing agent which is normally known to be suitable for the destruction of vitamin $B_{12}$ in that, in some cases, in the amounts employed in the releasing agent of the present invention, such reducing agents do not destroy vitamin $B_{12}$. As a result, such reducing agents are included within the scope of the present invention.

The cyanide ion component is provided by a suitable cyanide compound such as a cyanide salt; e.g., potassium cyanide.

The three components are employed in an amount effective to denature $B_{12}$ endogenous serum proteins and to release vitamin $B_{12}$ therefrom. In general, the ratio of reducing agent to organic liquid is from 0.00001:1 to 0.1:1, preferably from 0.00025:1 to 0.00075:1. The ratio of cyanide ion to organic liquid is generally from 0.00001:1 to 0.1:1, and preferably from 0.00025:1 to 0.00075:1 The selection of optimum amounts is deemed to be within the scope of those skilled in the art from the teachings herein.

The releasing agent may be employed as an aqueous solution of the organic liquid, reducing agent and cyanide ions. In such cases, the ratio of organic liquid to water is generally from 4:1 to 6:1.

The releasing agent is added to the serum in an amount effective to denature vitamin $B_{12}$-binding endogenous protein and to release vitamin $B_{12}$ therefrom. In general, the releasing agent is added to provide a ratio of organic liquid to serum of at least 0.5:1, and preferably at least 1.28:1, with the ratio of organic liquid to serum generally being no greater than 10:1. The use of excess amounts of releasing agent may adversely affect the subsequent $B_{12}$ assay, and as a result, the releasing agent is preferably not employed in quantities which are much greater than the effective minimum amount for release of vitamin $B_{12}$ from the endogenous binder.

The serum is contacted with the releasing agent for a time sufficient to release vitamin $B_{12}$ from endogenous binder. In general, the contacting time is about 15 minutes, although longer times could be employed. The vitamin $B_{12}$ may be released from endogenous binder at room temperature, although higher temperatures could be employed; e.g., up to 37° C.

The vitamin $B_{12}$ releasing agent may be incorporated into a kit for the assay of vitamin $B_{12}$ which includes, in addition to the releasing agent, a vitamin $B_{12}$ binder and a vitamin $B_{12}$ tracer. The kit may further include suitable standards, buffer(s) and an adsorbent for separating unbound $B_{12}$ and $B_{12}$ tracer, from $B_{12}$ and $B_{12}$ tracer bound to $B_{12}$ binder.

The vitamin $B_{12}$ binder may be either a naturally occurring binder or an antibody to vitamin $B_{12}$, produced by a procedure known in the art for raising antibodies. As representative examples of natural binders, there may be mentioned: saliva, chicken serum, intrinsic factor, etc., with intrinsic factor being preferred. The selection of a suitable binder is deemed to be within the scope of those skilled in the art from the teachings herein.

The binder may be unsupported or supported on a suitable support for use in a so-called solid phase assay. Thus, for example, the binder may be included in the kit adsorbed on or covalently bound to a solid support; e.g., a tube, solid particles, sheet, etc.

The vitamin $B_{12}$ tracer is vitamin $B_{12}$ or appropriate analog thereof (one which is specifically bound by the $B_{12}$ binder) labeled with a suitable "tag" or "label." The label or tag, as known in the art, may be a radioisotope, an enzyme or a fluorescent material. In general, the tracer is radiolabeled; in particular, $^{57}Co$. The tracer could also be a radioiodinated analog of vitamin $B_{12}$; e.g., as disclosed in U.S. Pat. No. 3,981,863.

In accordance with the vitamin $B_{12}$ assay, the serum is incubated with the releasing agent, preferably at room temperature for a time sufficient to denature the serum $B_{12}$ endogenous binders and release vitamin $B_{12}$ therefrom. Subsequently, the serum sample is diluted with a suitable buffer (the pH of the assay may vary over a wide range of pH), with such dilution minimizing the affect of the releasing agent components on the binder employed in the assay. The sample is contacted with vitamin $B_{12}$ tracer and binder, and the unbound tracer and $B_{12}$ is separated from the $B_{12}$ and tracer bound to the $B_{12}$ binder. In the case where the $B_{12}$ binder is not supported on a solid support, the free $B_{12}$ and free tracer may be separated by the use of a particulate adsorbent; e.g., dextran coated charcoal, ion exchange resin, etc.

The following example is illustrative of the invention; however, the scope of the invention is not to be limited thereby:

EXAMPLE

The following example of the assay is one in which the assay is performed at pH 9.3. It may also be done at any pH known in the art.

The following reagent kit is used in the assay.

1. Tracer 0.75 u Ci Vitamin $B_{12}$ [$^{57}Co$], human serum albumin, sodium borate, dextran and preservatives.

2. Binder

Hog Intrinsic Factor formulated for a trace binding of $55 \pm 15\%$, human serum albumin, dextran and preservatives.

3. Standards

Containing human serum albumin, sodium borate, sodium chloride and preservatives.

3A Standard A—Zero level
3B Standard B—100 pg/ml $B_{12}$
3C Standard C—200 pg/ml $B_{12}$
3D Standard D—400 pg/ml $B_{12}$
3E Standard E—1000 pg/ml $B_{12}$
3F Standard F—2000 pg/ml $B_{12}$ 4. Releasing Agent 82.5% Acetone: 17.5% water solution which contains 0.05% Potassium Cyanide and 0.05% dithiothreitol.

5. Buffer pH 9.3 Sodium Borate with 6.25 µg Potassium Cyanide/ml.

6. Dithiothreitol Solution 5%

6A. Assay Buffer

A mixture of 1 ml of Reagent 6 to 50 ml of Reagent 5.

7. Dextran Coated Charcoal Suspension $4.4 \pm 0.1$ G dextran charcoal dry mix (1:10), suspending agent and sodium chloride in 100 ml distilled water.

| PROTOCOL | |
|---|---|
| Preparation of a Standard Curve | Clinical Determinations |
| 1. Number 16 polypropylene tubes sequentially from 1–16. | 1. Starting with 17, consecutively number two polypropylene tubes for each clinical sample. |
| 2. Add Standards (Reagents 3A–3F) as follows: | 2. Add 100 µl patient sample to each of two tubes. Mix gently. |

| Tube No. | Standard | Vitamin $B_{12}$ as pg/ml |
|---|---|---|
| 3–6 | 100 µl A | 0 |
| 7, 8 | 100 µl B | 100 |
| 9, 10 | 100 µl C | 200 |
| 11, 12 | 100 µl D | 400 |
| 13, 14 | 100 µl E | 1000 |
| 15, 16 | 100 µl F | 2000 |

| | |
|---|---|
| 3. Add 150 µl of releasing reagent (reagent 4) to tubes 3–16. | 3. Add 150 µl releasing reagent (reagent 4) to all tubes. |
| 4. Incubate all tubes at room temperature for 15 minutes. | |
| 5. Add Assay Buffer (Reagent 6A) as follows: | 5. Add 1000 µl Assay Buffer (Reagent 6A) to each tube. |

| Tube No. | Buffer Volume |
|---|---|
| 1, 2 | 1600 µl |
| 3–16 | 1000 µl |

| | |
|---|---|
| 6. Add 100 µl Tracer (Reagent 1) | 6. Add 100 µl Tracer (Reagent 1) |

PROTOCOL -continued

| | |
|---|---|
| to all tubes. Mix gently by hand. Set tubes 1 and 2 aside at room temperature until Step 14. | to each tube. Mix gently by hand. |
| 7. Add 100 μl Binder (Reagent 2) to tubes 5-16. Gently vortex. | 7. Add 100 μl Binder (Reagent 2) to each tube. Gently vortex. |

From this point, all tubes are treated as follows:
8. Incubate at room temperature for 45 minutes from the time of the last addition of the binder. Cover the rack of tubes with aluminum foil to exclude light or keep in the dark.
9. Add 0.4 ml dextran-coated charcoal to tubes 3-16 and to all patient sample tubes (17, 18, etc.). Do not add to tubes 1 and 2. This reagent is "squirted" into each tube to obtain a uniform suspension in the reaction mixture.
10. Keep at room temperature for 10 minutes from the time of last addition in Step 9.
11. Centrifuge at a minimum of 1240 × g for 15 minutes, preferably in the cold. Shorter times may be sufficient in equipment of higher centrifugal force.
12. Consecutively number a set of clean tubes, beginning with 3.
13. Gently decant each clear supernatant into the similarly numbered tube prepared in Step 12. Maximal transfer is obtained by hitting the rims together. Avoid decanting over any charcoal to the counting tube. Discard the charcoal residues.
14. Count the radioactivity in the supernatants and tubes 1 and 2 in sequence for one or more minutes with a scintillation (gamma) counter.

The Standard Curve covers the range of 100 to 2000 pg/ml of Vitamin $B_{12}$. A "Blank" (tubes 3 and 4) is used to correct for background counts and radioactive tracer which is not adsorbed onto the charcoal.

This invention is particularly advantageous in that it permits release of vitamin $B_{12}$ from endogenous binders without the necessity of heating to elevated heat releasing temperatures. The ability to effect such release at lower temperatures; e.g., room temperature, shortens the overall assay procedure, and it eliminates the previous heating and cooling step required during such assays.

Numerous modifications and variations of the present invention are possible in light of the above teachings and, therefore, within the scope of the appended claims, the invention may be practiced otherwise than as particularly described.

We claim:

1. A process for the release of vitamin $B_{12}$ from endogenous serum binders, comprising:
 contacting serum containing vitamin $B_{12}$ bound to endogenous binders therefor with a vitamin $B_{12}$ releasing agent comprising a water miscible organic liquid solvent which does not destroy vitamin $B_{12}$, a reducing agent which does not destroy vitamin $B_{12}$, and cyanide ions, said releasing agent being employed in an amount effective to release vitamin $B_{12}$ from endogenous binders therefor to thereby eliminate the necessity for heating the serum to heat releasing temperatures.

2. The process of claim 1 wherein the ratio of reducing agent to organic liquid solvent is from 0.00001:1 to 0.1:1 and the ratio of cyanide ion to organic liquid solvent is from 0.00001:1 to 0.1:1.

3. The process of claim 2 wherein the organic liquid solvent is selected from the group consisting of ketones, alcohols, ethers, dimethylformamide and dimethylsulfoxide.

4. The process of claim 3 wherein the cyanide ion to organic liquid ratio is from 0.00025:1 to 0.00075:1 and the reducing agent to organic liquid ratio is from 0.00025:1 to 0.00075:1.

5. The process of claim 4 wherein the releasing agent is employed as an aqueous solution wherein the ratio of organic liquid to water is from 4:1 to 6:1.

6. The process of claim 4 wherein the releasing agent is employed in an amount to provide a ratio of organic liquid to serum of at least 0.5:1 and no greater than 10:1.

7. The process of claim 6 wherein the organic liquid is acetone and the reducing agent is dithiothreitol.

8. In an assay for vitamin $B_{12}$ wherein a serum sample is contacted with vitamin $B_{12}$ tracer and vitamin $B_{12}$ binder, the improvement comprising:
 initially releasing vitamin $B_{12}$ from endogenous binders therefor by contacting the serum with a vitamin $B_{12}$ releasing agent comprising a water miscible organic liquid solvent which does not destroy vitamin $B_{12}$, a reducing agent which does not destroy vitamin $B_{12}$, and cyanide ions, said releasing agent being employed in an amount effective to release vitamin $B_{12}$ from endogenous binders therefor to thereby eliminate the necessity for heating the serum to heat releasing temperatures.

9. The assay of claim 8 wherein the ratio of reducing agent to organic liquid solvent is from 0.00001:1 to 0.1:1 and the ratio of cyanide ion to organic liquid solvent is from 0.00001:1 to 0.1:1.

10. The assay of claim 9 wherein the organic liquid solvent is selected from the group consisting of ketones, alcohols, ethers, dimethylformamide and dimethylsulfoxide.

11. The assay of claim 10 wherein the cyanide ion to organic liquid ratio is from 0.00025:1 to 0.00075:1 and the reducing agent to organic liquid ratio is from 0.00025:1 to 0.00075:1.

12. The assay of claim 11 wherein the releasing agent is employed as an aqueous solution wherein the ratio of organic liquid to water is from 4:1 to 6:1.

13. The assay of claim 11 wherein the releasing agent is employed in an amount to provide a ratio of organic liquid to serum of at least 0.5:1 and no greater than 10:1.

14. The assay of claim 13 wherein the organic liquid is acetone and the reducing agent is dithiothreitol.

15. A kit for the assay of vitamin $B_{12}$, comprising:

vitamin B$_{12}$ tracer, vitamin B$_{12}$ binder and a vitamin B$_{12}$ releasing agent comprising a water miscible organic liquid solvent which does not destroy vitamin B$_{12}$, a reducing agent which does not destroy vitamin B$_{12}$, and cyanide ions, said releasing agent being employed in an amount effective to release vitamin B$_{12}$ from endogenous binders therefor without the necessity for heating a serum sample to heat releasing temperatures.

16. The kit of claim 15 wherein the ratio of reducing agent to organic liquid solvent is from 0.00001:1 to 0.1:1 and the ratio of cyanide ion to organic liquid solvent is from 0.00001:1 to 0.1:1.

17. The kit of claim 16 wherein the organic liquid solvent is selected from the group consisting of ketones, alcohols, ethers, dimethylformamide and dimethylsulfoxide.

18. The kit of claim 17 wherein the releasing agent is employed as an aqueous solution wherein the ratio of organic liquid to water is from 4:1 to 6:1.

19. The kit of claim 18 wherein the organic liquid is acetone and the reducing agent is dithiothreitol.

20. The kit of claim 16 wherein the vitamin B$_{12}$ tracer is radiolabeled vitamin B$_{12}$.

21. The kit of claim 20 wherein the vitamin B$_{12}$ tracer is vitamin B$_{12}$ [$^{57}$Co].

22. The kit of claim 21 wherein the vitamin B$_{12}$ binder is hog intrinsic factor.

23. The kit of claim 22 wherein the organic liquid is acetone and the reducing agent is dithiothreitol.

24. The kit of claim 23 wherein the releasing agent is employed as an aqueous solution wherein the ratio of acetone to water is from 4:1 to 6:1.

25. The kit of claim 24 wherein the cyanide ion to acetone ratio is from 0.00025:1 to 0.00075:1 and the dithiothreitol to acetone ratio is from 0.00025:1 to 0.00075:1.

26. The process of claim 1 wherein the contacting is effected at a temperature of less than 100° F.

27. The process of claim 26 wherein the contacting is effected at a temperature of from room temperature to 37° C.

28. The process of claim 1 wherein the reducing agent is selected from the group consisting of dithiothreitol, dithioerythritol, monothioglycol, thiodiglycol, thioglycollic acid, cysteine, homocysteine, glutathione, mercaptoethanol, sulfhydryl reducing agents, sodium sulfite, sodium dithionate, sodium sulfide and sodium metabisulfite.

29. The assay of claim 8 wherein the contacting is effected at a temperature of less than 100° F.

30. The assay of claim 29 wherein the contacting is effected at a temperature of from room temperature to 37° C.

31. The assay of claim 8 wherein the reducing agent is selected from the group consisting of dithiothreitol, dithioerythritol, monothioglycol, thiodiglycol, thioglycollic acid, cysteine, homocysteine, glutathione, mercaptoethanol, sulfhydryl reducing agents, sodium sulfite, sodium dithionate, sodium sulfide and sodium metabisulfite.

32. The kit of claim 17 wherein the reducing agent is selected from the group consisting of dithiothreitol, dithioerythritol, monothioglycol, thiodiglycol, thioglycollic acid, cysteine, homocysteine, glutathione, mercaptoethanol, sulfhydryl reducing agent, sodium sulfite, sodium dithionate, sodium sulfide and sodium metabisulfite.

* * * * *